United States Patent [19]

Lang et al.

[11] Patent Number: 5,143,937
[45] Date of Patent: Sep. 1, 1992

[54] BENZENESULFONAMIDES AND A PROCESS FOR THEIR PREPARATION

[75] Inventors: Hans-Jochen Lang, Hofheim am Taunus; Ernold Granzer, Kelkheim; Bela Kerekjarto, Hofheim am Taunus, all of Fed. Rep. of Germany

[73] Assignee: Hoechst Aktiengesellschaft, Frankfurt am Main, Fed. Rep. of Germany

[21] Appl. No.: 480,932

[22] Filed: Feb. 16, 1990

[30] Foreign Application Priority Data

Feb. 18, 1989 [DE] Fed. Rep. of Germany ....... 3905075

[51] Int. Cl.$^5$ .................. C07C 311/39; C07C 311/29; A61K 31/18
[52] U.S. Cl. ..................................... 514/603; 514/604; 514/824; 514/869; 564/83; 564/85; 564/89; 564/92
[58] Field of Search .................. 564/83; 514/603, 824, 514/864

[56] References Cited

U.S. PATENT DOCUMENTS

| | | | |
|---|---|---|---|
| 2,236,168 | 3/1941 | Dietrich ................................. | 564/92 |
| 3,165,550 | 1/1965 | Holland et al. ........................ | 564/83 |
| 3,678,039 | 7/1972 | Werner et al. .................. | 260/239.6 |
| 3,737,316 | 6/1973 | Salminen et al. .................... | 430/376 |
| 4,013,621 | 3/1977 | Knell ............................. | 260/45.9 R |
| 4,113,463 | 9/1978 | Oshio et al. ........................... | 564/85 |
| 4,849,444 | 7/1989 | Lang et al. ........................... | 514/425 |

FOREIGN PATENT DOCUMENTS

| | | |
|---|---|---|
| 0618769 | 4/1961 | Canada . |
| 2617180 | 11/1976 | Fed. Rep. of Germany . |
| 0010215 | 6/1967 | Japan . |
| 1031916 | 6/1966 | United Kingdom . |

OTHER PUBLICATIONS

Burmistrov et al. I "Oxidation Reduction Potentials," *2h Org. Khim.* 1977, 13(2) 378-80 abst. in CA 87(5):38533k.

Belov et al., "Degenerate Z,E-isomerization" *Zh Org. Khim* 1983 19(4) 825-7 abst. in CA 99(11): 87438q.

Roberts et al., "Studies in Peroxidase Action," *Tetrahydron* 23(3), 1335-9 (1967) abst. in CA 66(19) 35041d.

Burmistrov et al. I "Nature of the Effect" *2h Org. Khim* 1980, 16(7) 1487-94, abst. in CA 93(23) 220269e.

Statsek et al., "Toxicology of New Polymer Stabilizers" *Gig Primen Polim. Mater Izdelii Nikh.* 1969, No. 1, 314-22 abst. in CA75(17):107790h.

Chemical Abstracts, vol. 93, p. 484, 220269e, (1980).

Chemical Abstracts, vol. 75, p. 231, 107790h, (1971), 9734.

*Primary Examiner*—Richard L. Raymond
*Assistant Examiner*—P. G. O'Sullivan
*Attorney, Agent, or Firm*—Finnegan, Henderson, Farabow, Garrett and Dunner

[57] ABSTRACT

Compounds of the formula I

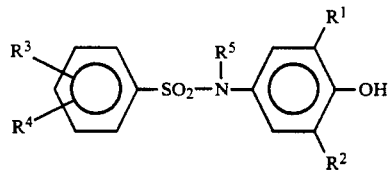

where $R^1$ to $R^5$ have the meaning indicated, a process for their preparation and their use as medicaments are described. They are effective lipid-lowering agents with antioxidative properties from the benzenesulfonamide series. They do not have hypotensive and diuretic properties.

4 Claims, No Drawings

BENZENESULFONAMIDES AND A PROCESS FOR THEIR PREPARATION

DESCRIPTION

The invention relates to benzenesulfonamides.

It is known that benzenesulfonamides of the formula IV

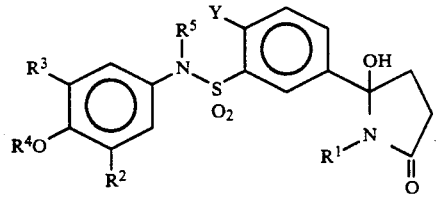

have diuretic and hypotensive properties and at the same time are able to lower the atherogenic lipids of the LDL fraction in the serum (German Offenlegungsschrift 3,713,757 corresponding to EP-A-0,288,028 and U.S. Pat. No. 4,849,444).

For hyperlipidemics, who are not suffering from hypertonia and/or cardiac insufficiency at the same time, the diuresis and the lowering of blood pressure proves disturbing.

The invention is based on the object of making available benzenesulfonamide derivatives which have neither diuretic nor hypotensive action.

It has been found that the diuretic and hypotensive properties are no longer present in benzenesulfonamides of the formula I

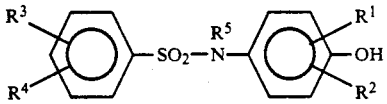

The therefore relates to benzenesulfonamides of the formula I, in which $R^1$ is alkyl having 1-5 carbon atoms or cycloalkyl having 3 to 5 ring members, $R^2$ is branched alkyl having 3 to 5 carbon $R^3$ is hydrogen, halogen, alkyl or alkoxy in each case having 1-4 carbon atoms, $R^4$ is hydrogen, alkyl having 1-3 carbon atoms, halogen, trifluoromethyl, a radical $-SO_n-A$, in which A is alkyl having 1 to 3 carbon atoms or, if $n=2$, is $NR^6R^7$ with $R^6$ and $R^7$ being hydrogen or alkyl having 1 to 4 carbon atoms, $n=0$, 1 or 2, and $R^5$ hydrogen or alkyl having 1-3 carbon atoms.

The alkyl radicals in the substituents $R^1$, $R^3$, $R^4$ and $R^5$ and also $R^6$ and $R^7$ are straight-chain or branched. The same applies to the alkoxy radical. Halogen stands for fluorine, chlorine, bromine and iodine, preferably for chlorine.

The invention relates in particular to the compounds of the formula I for use as pharmaceuticals.

Preferred compounds of the general formula I are those in which $R^1$ is methyl, isopropyl or tert.-butyl, $R^2$ is isopropyl or tert.-butyl, $R^3$ is hydrogen, chlorine, or straight-chain or branched alkoxy having 1 to 3 carbon atoms, $R^4$ is trifluoromethyl or a radical $-SO_n-A$, in which A and n have the abovementioned meanings, and $R^5$ hydrogen or alkyl having 1-3 carbon atoms.

The following compounds of the formula I are particularly preferred:

5-N-(3,5-di-tert.-butyl-4-hydroxyphenylsulfamoyl)-2-chlorobenzene-N,N-dimathylsulfonamide 5-N-(3,5-di-tert.-butyl-4-hydroxyphenylsulfamoyl)-2-chlorobenzene-N-methylsulfonamide 5-N-(3,5-di-tert.-butyl-4-hydroxyphenylsulfamoyl)-2-chlorobenzenesulfonamide 3-N-(3,5-di-tert.-butyl-4-hydroxyphenylsulfamoyl)-4-chlorobenzenesulfonamide.

The invention furthermore relates to a process for the preparation of the compounds of the formula I, which comprises reacting compounds of the formula II

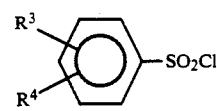

with an amine of the formula III

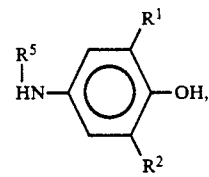

in which $R^1$ to $R^5$ have the meaning indicated, and, if appropriate, converting the resulting compounds of the formula I, in which $R^5$ is hydrogen, into compounds of the formula I, in which $R^5$ is an alkyl radical with 1-3 carbon atoms, by customary alkylation.

The compounds of the formula II are made to react in a manner known per se with an aminophenol of the structure III, in which $R_1$ to $R_5$ have the meaning indicated, with formation of the compounds I. The reaction is preferably carried out in this case by allowing both reactants to react in a molar ratio of 1:1 in water or an inert polar organic solvent, such as dimethylformamide, dimethylacetamide, dioxane, tetrahydrofuran, diethylene glycol dimethyl ether, in lower alcohols having 1-4 carbon atoms, for example in methanol, ethanol or isopropanol, and also in an alkanoic acid lower alkyl ester, for example methyl acetate or ethyl acetate.

The presence of at least 1, better of 2 or more, moles of a suitable proton-scavenging auxiliary base, such as, for example, an alkali metal hydroxide or an alkaline earth metal hydroxide such as KOH, NaOH or Ca(OH)$_2$, an alkali metal carbonate or hydrogen carbonate such as Na$_2$CO$_3$, K$_2$CO$_3$, NaHCO$_3$ or KHCO$_3$ or, preferably, a tertiary amine such as trimethylamine, triethylamine, tripropylamine, tributylamine, dicyclohexylethylamine or pyridine, but also alkali metal and alkaline earth metal salts of weak alkanecarboxylic acids such as, for example, sodium acetate proves advantageous.

The sulfonyl chlorides of the formula II and the aminophenols of the formula III, in which $R^1$ to $R^5$ have the meaning indicated, are largely known from the literature and, if not known, can be obtained in analogy to the known processes.

The process products are useful pharmaceuticals and are distinguished by very favorable therapeutically utilizable properties.

The invention therefore also relates to pharmaceutical preparations based on compounds of the formula I, and to their use as pharmaceuticals, in particular for the treatment of disorders of lipid metabolism. The invention further relates to the use of compounds of the formula I for the production of pharmaceuticals.

According to contemporary opinion, elevated VLDL and LDL levels are substantially involved in the formation and the progress of atherosclerosis. Oxidized LDL, in particular, is strongly atherogenic and cytotoxic. The lowering of elevated VLDL and LDL levels and the prevention of pathophysiological oxidation processes for influencing atherosclerotic processes is therefore of great therapeutic interest. In a number of patients, an elevated blood pressure additionally plays an important role. For these patients, benzenesulfonamides have been described (DE-A-3,713,757) which have diuretic and hypotensive properties and at the same time are able to lower the atherogenic lipids of the LDL fraction in the serum. However, for patients who do not suffer from hypertonia and/or cardiac insufficiency but have elevated lipid levels, diuresis and lowering of blood pressure are disturbing. The sulfonamides of the formula I according to the invention are distinguished by their novel quality of action, since diuretic and hypotensive properties are no longer present. The novel compounds are able to lower the atherogenic lipids to a substantially larger extent and can prevent oxidative processes. They therefore fulfil the requirements as pharmaceuticals for the regulation of the blood lipids of hyperlipidemics who do not have high blood pressure and do not suffer from cardiac insufficiency. Moreover, the substances may be useful pharmaceuticals in the treatment of diseases in which oxidative processes play a role. The fact that it was possible to achieve this quality of action with compounds from the benzenesulfonamide class which, not least because of their good tolerability, are included in the base therapeutics, is of great importance.

From numerous publications in recent years, it follows that injuries to the vascular endothelium precede the formation of atherosclerotic plaques. Endothelial injuries of this type can be caused by fatty acid peroxides and radical reactions of active oxygen species so that a reduction of the atherogenic risk is inevitably associated with a reduction of these lipid peroxides, which are essentially transported in the LDL fraction.

It has now been possible to show that the active compounds according to the invention are able to lower the LDL fraction even in the range from 1-10 mg/kg in the rat without influencing the HDL fraction. Moreover, the compounds according to the invention inhibit lipid peroxidation, which can be regarded as a measure of the formation of atherogenic oxidized LDL (inhibition of NADPH-dependent microsomal lipid peroxidion, malondialdehyde formation $IC_{50} \leq 1 \mu M$).

The compounds I are administered in doses of at least 0.5 mg/kg and day, preferably 1.0 mg/kg/day, up to 15 mg/kg/day, preferably 10 mg/kg/day, based on an adult human of body weight about 75 kg.

Suitable therapeutic preparations of the novel compounds are, in particular, tablets, coated tablets, capsules, juices and suppositories and also ampoules for parenteral administration (i.v., s.c. and i.m.). The compounds of the formula I can in this case either be administered alone or with pharmacologically acceptable excipients. A form for oral administration is preferred. For this purpose, the active compounds are preferably mixed with substances which are known per se and, by methods which are known per se, brought into suitable forms for administration, such as tablets, hard gelatin capsules, aqueous or oily suspensions or aqueous or oily solutions. Inert excipients which may be used are, for example, magnesium carbonate, lactose or maize starch with the addition of other substances such as, for example, magnesium stearate. In this case, the preparation can be carried out as dry or moist granules. Possible oily excipients or solvents are, particularly, vegetable and animal oils, such as, for example, sunflower oil or cod liver oil.

In the treatment of lipid metabolism disturbances, in addition to the customary fillers and excipients, the preparations may further contain an antihypertensive, such as, for example, a saluretic, reserpine, hydralazine, guanethidine, α-methyldopa, clonidine or a β-sympatholytic, or an antihyperuremic agent, an oral antidiabetic, a geriatric or an agent having a circulation-increasing action.

In the following examples, the melting and decomposition points of the exemplary embodiments are not corrected.

EXAMPLE 1–45

General procedure for the preparation of the compounds of the formula I:

A suspension or solution of 0.1 to 0.2 mol of aminophenol III in 450 ml of ethyl acetate is added in portions to a solution of 0.1 mol of sulfonyl chloride II and 0.3 mol of triethylamine in 500 ml of ethyl acetate. The temperature is kept between 30° and 40° C. The mixture is stirred at 50° C. for 3 hours and cooled, water is added, the organic phase is separated off and the aqueous phase is extracted several times with ethyl acetate. The combined organic phases are washed with water and dried over sodium sulfate and the solvent is removed by distillation. Further purification is by crystallization.

TABLE 1

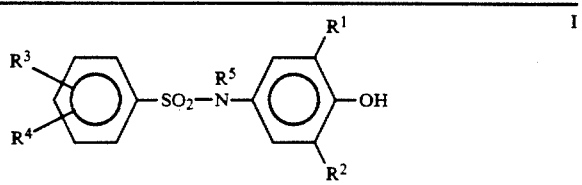

| Example | $R^1$ | $R^2$ | $R^4$ | $R^3$ | $R^5$ | m.p. |
|---|---|---|---|---|---|---|
| 1 | t-But | t-But | 3-$H_2NO_2S$— | 4-Cl | H | 217° C. |
| 2 | i-Prop | i-Prop | 3-$H_2NO_2S$— | 4-Cl | H | 210° C. |
| 3 | t-But | t-But | 3-$H_2NO_2S$— | 4-Cl/6-$NH_2$ | H | 238° C. |

TABLE 1-continued

Structure I:
3,5-substituted benzenesulfonamide with R³, R⁴ on left benzene ring (SO₂-N(R⁵)-) linked to right phenol ring with R¹, R² and OH.

| Example | R¹ | R² | R⁴ | R³ | R⁵ | m.p. |
|---|---|---|---|---|---|---|
| 4 | t-But | t-But | H | H | H(K) | 180–181° C. |
| 5 | t-But | t-But | 4-Cl | H | H(K) | 203–205° C. |
| 6 | t-But | t-But | 2-Cl | 5-NH₂ | H | 208–209° C. |
| 7 | t-But | t-But | 4-Me | H | H(K) | 177° C. |
| 8 | t-But | t-But | 2-Cl | 6-Cl | H | 190° C. |
| 9 | i-Prop | i-Prop | H | H | H | 145–146° C. |
| 10 | i-Prop | i-Prop | 4-Me | H | H | 158° C. |
| 11 | i-Prop | i-Prop | 4-Cl | H | H | 163° C. |
| 12 | Me | t-But | 3-H₂NO₂S— | 4-Cl | H | 152° C. |
| 13 | Me | t-But | 4-Me | H | H | 170° C. |
| 14 | Me | t-But | H | H | H | 136° C. |
| 15 | Me | t-But | 4-Cl | H | H | 153° C. |
| 16 | t-But | t-But | 4-H₂NO₂S— | H | H | 191° C. |
| 17 | t-But | t-But | 3-H₂NO₂S— | H | H | 225° C. |
| 18 | t-But | t-But | 3-MeNHO₂S— | 4-Cl | H | 179° C. |
| 19 | t-But | t-But | 3-Me₂NO₂S— | 4-Cl | H | 170° C. |
| 20 | t-But | t-But | 3-H₂NO₂S— | 4-Me | H | 166–168° C. |
| 21 | t-But | t-But | 3-(NH—SO₂—pyridyl) | 4-Cl | H | 191° C. |
| 22 | t-But | t-But | 5-H₂NO₂S | 2-Cl | H | 201° C. |
| 23 | t-But | t-But | 3-MeS— | H | H | 158–160° C. |
| 24 | t-But | t-But | 4-Me—S— | H | H | 193–195° C. |
| 25 | t-But | t-But | 3-Me—SO— | H | H | 187° C. |
| 26 | t-But | t-But | 3-Me—SO₂— | H | H | 177–178° C. |
| 27 | t-But | t-But | 4-MeSO— | H | H | 219° C. |
| 28 | t-But | t-But | 2Me—S— | H | H | 135° C. |
| 29 | t-But | t-But | 2-Me—SO₂ | H | H | 223° C. |
| 30 | t-But | t-But | 4-CF₃— | H | H | 182–183° C. |
| 31 | t-But | t-But | 3-CF₃ | 4-Cl | H | 135° C. |
| 32 | t-But | t-But | 3-CF₃ | H | H | 144–145° C. |
| 33 | t-But | t-But | 2-CF₃ | H | H | 129–131° C. |
| 34 | t-But | t-But | 5-CF₃ | 2-Cl | H | 192° C. |
| 35 | i-Prop | i-Prop | 3-CF₃ | 4-Cl | H | 178° C. |
| 36 | i-Prop | i-Prop | 3-MeSO₂— | H | H | 159° C. |
| 37 | Me | t-But | 3-CF₃ | H | H | 134–135° C. |
| 38 | Me | t-But | 4-CF₃ | H | H | 162° C. |
| 39 | t-But | t-But | 3-Et—N(H)—SO₂— | 4-Cl | H | 164° C. |
| 40 | t-But | t-But | 3-iPropN(H)—SO₂— | 4-Cl | H | 187° C. |
| 41 | t-But | t-But | 4-H₂NO₂S | 3-Cl | H | 185° C. |
| 42 | t-But | t-But | 4-OMe | H | H | 197–200° C. |
| 43 | t-But | t-But | 5-Me₂NO₂S— | 2Cl | H | 215° C. |
| 44 | t-But | t-But | 3-H₂N—O₂S— | 4-MeO— | H | 214–215° C. |
| 45 | t-But | t-But | 3-Me₂NO₂S— | 4-Cl | H | 321–134° C. |

We claim:

1. A benzenesulfonamide selected from the group consisting of

5-N-(3,5-di-tert.-butyl-4-hydroxyphenylsulfamoyl)-2-chlorobenzene-N,N-dimethylsulfonamide, 5-N-(3,5-di-tert.-butyl-4-hydroxyphenylsulfamoyl)-2-chlorobenzene-N-methylsulfonamide, 5-N-(3,5-di-tert.-butyl-4-hydroxyphenylsulfamoyl)-2-chlorobenzenesulfonamide, or 3-N-(3,5-di-tert.-butyl-4-hydroxyphenylsulfamoyl)-4-chlorobenzenesulfonamide.

2. A method for the treatment of a hyperlipidemic which comprises administering an effective amount of a compound as claimed in claim 1.

3. A pharmaceutical composition comprising an effective amount of a compound as claimed in claim 1 and pharmaceutically customary additives.

4. A method for the treatment of a hyperlipidemic which comprises administering a composition as claimed in claim 3.